United States Patent
Kato et al.

(10) Patent No.: US 6,470,201 B2
(45) Date of Patent: Oct. 22, 2002

(54) AUTOMATIC ELECTROPHYSIOLOGICAL MEASURING APPARATUS / METHOD

(75) Inventors: Hirokazu Kato, Hatoyama (JP); Jun Otomo, Tokyo (JP); Sayuri Nomura, Higashimatsuyama (JP); Tomoko Takeshita, Higashimatsuyama (JP); Sakae Saito, Tokorozawa (JP); Shokichi Matsunami, Tokorozawa (JP); Noboru Moriya, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 53 days.

(21) Appl. No.: 09/799,119

(22) Filed: Mar. 6, 2001

(65) Prior Publication Data
US 2001/0011154 A1 Aug. 2, 2001

Related U.S. Application Data

(62) Division of application No. 09/740,817, filed on Dec. 21, 2000.

(30) Foreign Application Priority Data

Dec. 24, 1999 (JP) ............................................ 11-366242

(51) Int. Cl.$^7$ .......................... A61B 5/05; G01N 33/53; G01N 27/26; C12M 1/34; C12Q 1/00
(52) U.S. Cl. .......................... 600/345; 435/4; 435/7.1; 435/287.1; 204/400; 204/408; 204/403.01
(58) Field of Search ................................. 600/345, 300, 600/346, 347; 435/4, 7.1, 287.1; 204/400, 408, 403.01

(56) References Cited

U.S. PATENT DOCUMENTS 6,048,722 A * 4/2000 Farb et al. ................ 435/286.5
6,268,121 B1 * 7/2001 Takeshita et al. .......... 204/400

FOREIGN PATENT DOCUMENTS

JP 11-083785 3/1999

\* cited by examiner

*Primary Examiner*—Kevin Shaver
*Assistant Examiner*—Navin Natnithithadha

(57) ABSTRACT

An automatic electrophysiological measuring apparatus to automatically penetrate a glass electrode(s) into the membrane of a Xenopus Oocyte to hold the membrane potential and to automatically measure reactions to the administration of a medicine is to be provided.

A glass electrode 103 in the air is moved toward a Xenopus Oocyte 601 held in a cell. Changes in the potential states of the glass electrodes are picked up by a control computer to distinguish the relative positions of the glass electrode 102 and the Xenopus Oocyte 601 and the sequence of electrophysiological measurement so as to penetrate the glass electrode 102 into the Xenopus Oocyte 601, hold the membrane potential and automatically administer the medicine.

1 Claim, 8 Drawing Sheets

AUTOMATIC ELECTROPHYSIOLOGICAL MEASURING APPARATUS / METHOD

This is a division of application Ser. No. 09/740,817 field Dec. 21, 2000.

BACKGROUND OF THE INVENTION

The present invention relates to an automatic electrophysiological measuring apparatus and method using Xenopus Oocytes.

The science of inquiring into the electrical properties of living organisms is known as "electrophysiology," which has some 200 years' history and has developed as one of the main areas of physiology. Especially in nerves and muscles, the action potential is the most essential event. As it has been revealed that the conduction of excitement is mediated by an electric current, electrophysiology has become one of the most important fields of study for physiologists.

The voltage clamp method was proposed by Cole of the United States in the 1940s. This is a method to keep the membrane potential constant all the time by using at the moment of fluctuation of the membrane potential a feedback circuit which flows an electric current in the direction of suppressing the membrane potential. This voltage clamp method made possible quantitative measurement of the relationship between the membrane potential and ion permeability, and Hodgikin, Huxley and Katz of the United Kingdom used this voltage clamp method to analyze the nature of the membrane conductance of giant axons of Loligo, and made many achievements which would constitute the basis of subsequent studies in neurobiology.

These achievements are reported by Hodgikin, A. L., Huxley, A. F. and Katz in the *Journal of Physiology*, No.116(1952), pp. 424–44.

This method was further sophisticated by Neher and Sackman subsequently. They succeeded in measuring on a real time basis a current flowing from a live cell to a single-channel molecule. This technique, known as the patch clamp method, is described in detail by Sackman, B. and Neher, E. (eds.), *Single-Channel Recording* (2nd ed.), Plenum Press, New York (1995).

The central part of a hard glass capillary tube of about 1 mm in diameter is softened by heating with a heater, quickly extended in its lengthwise direction and pulled off to prepare an electrode for recording electric signals. A piece whose pulled-off tip is open and whose diameter is no greater than 1 $\mu$m is selected, filled inside with a 3M potassium chloride (KCl) solution by injection, and used as the electrode. By manually penetrating this electrode into each cell, the membrane potential of the cell can be measured.

Most of hormones and other nerve-carried substances convey information to cells via receptors known as seven transmembrane receptors or G protein-coupled receptors. The rapid progress of the Human Genome Project in recent years has resulted in a vast accumulation of information on the base sequences of genes, and it is presumed that there are many so-called "orphan" receptor genes, whose ligands are unidentified.

The ligands of seven transmembrane receptors are diverse, including hormones, signal transducing substances, cytokine and enzymes, and their molecular variety includes amines, amino acids, peptides, proteins, lipids, nucleic acids and ions. Furthermore, sensory receptors for light, smell and taste are a sort of seven transmembrane receptors, which play an important role in controlling the functions of living organisms. For this reason and because of their deep involvement in diseases, seven transmembrane receptors have been made a major target of powerful medicines. Actually, many of commercially available pharmaceuticals manifest their intended effects when combined with seven transmembrane receptors. Electrophysiometry also provides an important means for screening and determining the ligands of such orphan receptors.

Electrophysiometry is one of the few techniques available for real time measurement of the functions of membrane protein molecules, providing a central approach to receptor proteins. Therefore, electrophysiometry also is an indispensable tool for the development of pharmaceuticals, and its importance is expected to further increase in the future.

The Japanese Published Unexamined Patent Application No. Hei 11-083785 discloses a technique by which Xenopus Oocytes are caused to express histamine receptors, the response of Xenopus Oocytes to histamine is measured, and allergic reactions are detected tissue-specifically.

As stated above, electrophysiometry is indispensable for research on ion channels and the development of pharmaceuticals. However, electrophysiological experiments involve the problem of many troublesome procedures that have to be done manually. First, the worker should prepare glass microelectrodes each with a pulled-off tip whose diameter is no greater than 1 $\mu$m by heating and stretching a glass capillary tube. Furthermore, in order to penetrate the glass electrodes into a cell, a micromanipulator should be operated manually.

The micromanipulator, which is an apparatus to hold a glass electrode and manually control minute displacements of the glass electrode, involves the problem of requiring a high level skill to operate. Usually, penetration of a glass electrode into a cell is accomplished by manual operation with a micromanipulator. For this reason, since the glass electrode was devised in the 1940s until even today, electrophysiological measurement has depended heavily on the worker's craftsmanship.

A breakthrough in the automation of the penetration of Xenopus Oocytes by a glass electrode according to the prior art might be found in the application of image recognition. It is conceivable to determine the position of the membrane surface of a Xenopus Oocyte is determined with a CCD camera from above, and move the glass electrode, driven by a motor or otherwise, to penetrate the oocyte. However, when it is penetrated by the glass electrode, as the membrane surface of the Xenopus Oocyte would be subject to elastic deformation, it would be extremely difficult to check by image recognition from above whether or not the membrane has been accurately penetrated by the glass electrode. Moreover, control of the penetration of the glass electrode by image recognition is an extremely expensive and accordingly unrealistic means of control.

Since current variation responses in an electrophysiological experiment using Xenopus Oocytes or cultured cells may greatly fluctuate from cell to cell, it is necessary to increase the reliability of the data thereby obtained by averaging current responses from many cells. Therefore, in order to obtain fully reliable data, in the electrophysiological experiments each worker should carry out the penetration of a glass electrode into cells many times, resulting in the problem that acquisition of reliable data has to take a long time and a great amount of labor.

SUMMARY OF THE INVENTION

An object of the present invention, therefore, is to provide an automatic electrophysiological measuring apparatus and method using Xenopus Oocytes for automatically measuring responses of the cells to the administration of a medicine according to electric signals from a glass electrode penetrating the membranes of the Xenopus Oocytes membrane whose potential is fixed.

The automatic electrophysiological measuring apparatus according to the invention automatically carries out electrophysiological measurement regarding Xenopus Oocytes held in each of a plurality of cells (e.g. 8×12=96 cells) of a container in which a grounding electrode is arranged or formed by holding and moving the container to position the Xenopus Oocyte in each cell by shifting an XY stage, penetrating the Xenopus Oocyte in each cell with one or two glass electrodes with an inserting means, detecting electric signals emitted from the glass electrode(s) with a detecting means, fixing the membrane potential of the Xenopus Oocytes to a prescribed value with a fixing means, and administering a chemical substance to the Xenopus Oocytes with a microsyringe.

In order to accomplish electrophysiological measurement automatically, the XY stage, inserting means, fixing means and microsyringe are controlled by a control means. The control means detects and distinguishes the contact of the glass electrode(s) with the solution surface in the cell and with the membrane surface of the Xenopus Oocyte and the penetration of the glass electrode(s) into the membrane of the Xenopus Oocyte, controls its (their) penetration into the Xenopus Oocyte and the administration of the chemical substance to the Xenopus Oocyte with the microsyringe, and thereby makes possible automation of the electrophysiological measuring apparatus. Thus, automatic measurement is carried out by measuring the resistance(s) of the glass electrode(s), adjusting the zero-point potential (s) of the glass electrode (s), vibrating the glass electrode(s), controlling the fixation of the membrane potential and administering the chemical substance.

Each cell is shaped in a cone having a semisphere at the tip to hold a Xenopus Oocyte efficiently.

More preferably, the automatic electrophysiological measuring apparatus should be shielded from electromagnetic waves with a shielding means. Also, an optical microscope may be arranged to optically monitor the Xenopus Oocytes held in the cells.

The grounding electrode is molded of an electroconductive metal, with its surface coated with silver chloride, and a grounding wire is individually attached to each cell. The container is molded of agar, with part of which the grounding electrode is brought into contact to make it possible to uniformly ground the plurality of cells. Alternatively, the grounding electrode may as well be moved on a single axis in the solution held in the cell to ground each cell independently of others.

More specifically Xenopus Oocyte holding plates, in each of whose cells 8×12=96 Xenopus Oocytes are regularly arranged, are mounted on the XY stage. To each cell in which one Xenopus Oocyte is held, a grounding electrode is independently attached. One Xenopus Oocyte positioned by the XY stage at the center of the field of vision of a stereoscopic microscope is automatically penetrated by two glass electrodes by a motor-driven movement. The XY stage, the motor to drive the glass electrodes, the motor to drive the microsyringe for administering the ligand and the electrophysiological measuring apparatus are collectively controlled from outside by a control computer on the basis of electric signals from the glass electrodes, and automatic electrophysiological measurement regarding the plurality of Xenopus Oocytes is thereby enabled. The measured responses of the Xenopus Oocytes to the current are recorded by a measurement recording computer.

By the automatic electrophysiological measuring method according to the invention, electrophysiological measurement regarding Xenopus Oocytes is automatically carried out by holding on an XY stage a container having a plurality of cells each holding a Xenopus Oocyte, in each of the cells a grounding electrode being arranged or formed, moving the XY stage to position the Xenopus Oocyte in a prescribed cell, penetrating one or two glass electrodes into the Xenopus Oocyte in the prescribed cell, detecting electric signals emitted from the glass electrode(s), fixing the membrane potential of the Xenopus Oocyte to a prescribed value, and administering a chemical substance to the Xenopus Oocyte with a microsyringe. In order to accomplish electrophysiological measurement automatically, the movement of the XY stage, the penetration of the glass electrode(s) into the Xenopus Oocyte, the fixation of the membrane potential of the Xenopus Oocyte and the administration of the chemical substance to the Xenopus Oocyte are controlled on the basis of electric signals emitted from the glass electrode(s). These controls are accomplished by detecting and distinguishing the contact of the glass electrode(s) with the solution surface in the cell and with the membrane surface of the Xenopus Oocyte and the penetration of the glass electrode(s) into the membrane of the Xenopus Oocyte, thereby making possible automation of the electrophysiological measuring apparatus.

According to the invention, there is provided an automatic electrophysiological measuring apparatus which automatically penetrates glass electrodes into Xenopus Oocytes membranes, holds the membrane potentials and automatically measures reactions to the administration of a medicine. The principle of the invention will be explained below with reference to FIG. 3. First, a glass electrode 103 in the air is moved toward a Xenopus Oocyte 601 held in a cell. When the glass electrode 103 comes into contact with a solution surface 603 to become electrically connected to a grounding electrode 604, the potential of the glass electrode points to around 0 mV. When the glass electrode 103 is further moved to come into contact with the membrane surface of the Xenopus Oocyte 601, the potential of the glass electrode 103 points to around −5 mV. Further, as the other glass electrode 102 is moved to penetrate the membrane, its potential points to around −20 mV. These changes in the potentials of the glass electrodes are picked up by the control computer to identify the relative positions of the glass electrode 102 and the Xenopus Oocyte 601 to automate the sequence of electrophysiological measuring to penetrate the glass electrode 102 into the Xenopus Oocyte 601, hold its membrane potential and administer the medicine.

The automatic electrophysiological measuring apparatus according to the invention using Xenopus Oocytes can enhance the reliability of acquired data by automating the electrophysiological measurement and increasing the frequency of measurement while reducing the workload on the measuring personnel. Automation also enables the measurement of many samples to be accomplished at high speed and the processing of many tasks of electrophysiological measurement in a short period of time. Furthermore, it enables the unknown function of a gene whose base sequence is already known to be screened.

BRIEF DESCRIPTION OF THE DRAWINGS

Other objects and advantages of the invention will become apparent during the following discussion of the accompanying drawings, wherein.

DESCRIPTION OF THE PREFERRED EMBODIMENTS

Figure 1:
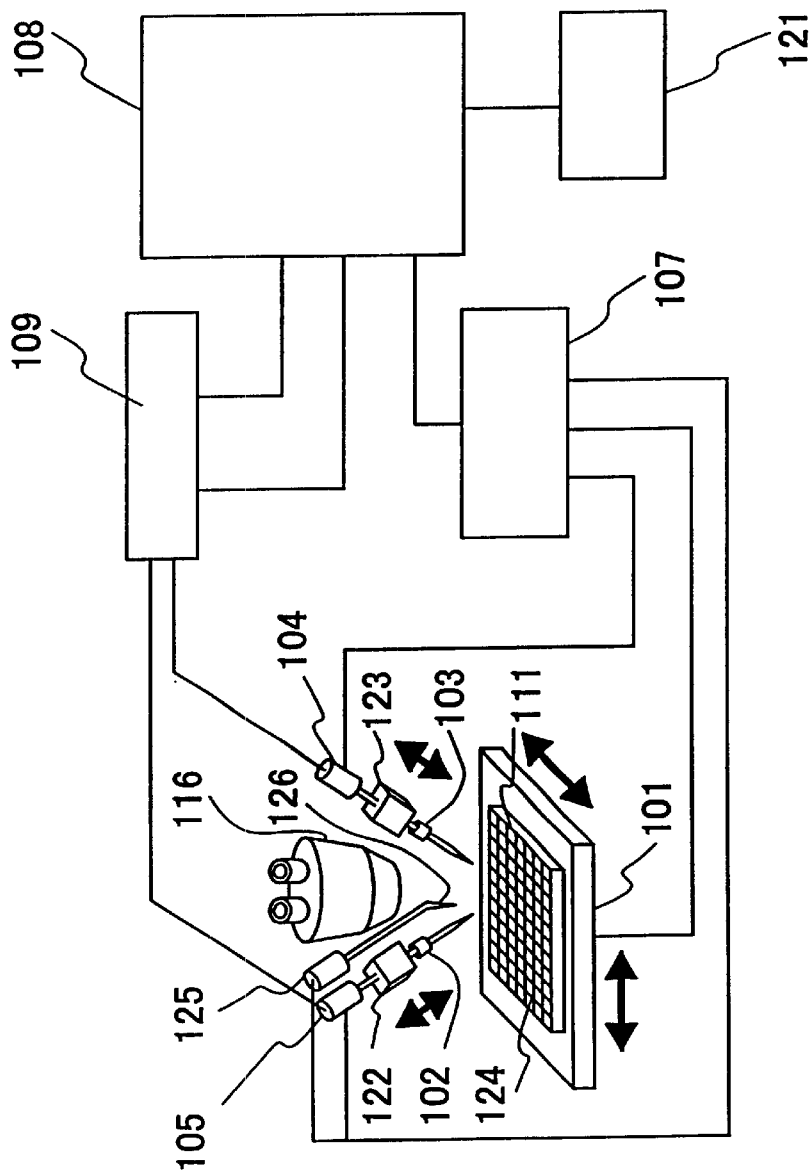
FIG. 1 illustrates an example of configuration of an automatic electrophysiological measuring apparatus embodying the present invention.

FIG. 1 illustrates an example of configuration of an automatic electrophysiological measuring apparatus embodying the present invention. The automatic electrophysiological measuring apparatus so embodying the invention consecutively and automatically measures the responses of a plurality of cells by electrophysiometry.

As shown in FIG. 1, the automatic electrophysiological measuring apparatus according to the invention consists of a stereoscopic microscope 116 for observing Xenopus Oocytes; glass electrodes 102 and 103 for penetrating the Xenopus Oocytes; micro-electric signal amplifying circuits 122 and 123 for amplifying micro-electric signals; a ligand administering microsyringe 126 for administering a ligand to the Xenopus Oocytes; an XY stage 101 for holding the stereoscopic microscope 116 and the glass electrodes 102 and 103; 96 well Xenopus Oocyte holding plates 111 each having 96 (cell) wells for holding the Xenopus Oocytes; a grounding electrode 124 for each 96 well plate; an electrophysiological measuring circuit 109 for measuring electric signals representing the potential states and the resistance states of the glass electrodes 102 and 103; a motor drive controller 107 for controlling the drive of motors for moving the XY stage 101 and the glass electrodes 102 and 103; a measurement recording computer 121 for recording the measurements; and a control computer 108 for controlling the electrophysiological measuring circuit 109, the motor drive controller 107 and the measurement recording computer 121.

The stereoscopic microscope 116 is so arranged over the XY stage 101 that its optical axis be vertical. The glass electrodes 102 and 103 respectively driven by motors 104 and 105 are symmetrically arranged in positions inclined by 30 degrees with respect to the vertical axis on which the stereoscopic microscope 116 is disposed. The whole apparatus is shielded to reduce noise and carry out electrophysiological experiments efficiently.

In this embodiment, Xenopus Oocytes injected with a human histamine receptor gene a few days ago are used. These Xenopus Oocytes are held by the 96 well Xenopus Oocyte holding plates 111. The 96 Xenopus Oocytes expressing the human histamine receptor are regularly arranged on the matrix of 8×12=96.

The positions of the glass electrodes 102 and 103 are so adjusted that they can penetrate the Xenopus Oocyte in one of the cells positioned at the center of the field of vision of the stereoscopic microscope 116.

Under the control of the control computer 108, the glass electrode driving motors 104 and 105 are driven, each on a single axis (as indicated by arrows in FIG. 1), to enable the glass electrodes 102 and 103 to penetrate the Xenopus Oocyte positioned at the center of the field of vision of the stereoscopic microscope 116.

The process of penetration of the cell membrane by the glass electrodes 102 and 103 can be visually observed through the stereoscopic microscope 116. It is also possible to equip the stereoscopic microscope 116 with a CCD camera to monitor the penetration of the Xenopus Oocyte by the glass electrodes 102 and 103, and control the movements of the glass electrodes 102 and 103 by image processing.

Incidentally, the stereoscopic microscope 116 is not an absolutely required constituent for penetration of Xenopus Oocytes by the glass electrodes 102 and 103, but is merely intended for visual confirmation of the actions of the glass electrodes 102 and 103. Therefore, the stereoscopic microscope 116 can be eliminated from the apparatus if the accuracy of the moving mechanism for the glass electrodes 102 and 103 is enhanced to enable them to penetrate Xenopus Oocytes without requiring visual confirmation.

The ligand administering microsyringe 126, as it is held by the micro-electric signal amplifying circuit 122 through a support 127, can be moved by the glass electrode driving motor 105 together with the glass electrode 102. When the glass electrode 102 enters the membrane of the Xenopus Oocyte, the tip of the ligand administering microsyringe 126 is adjusted to be positioned sufficiently close to the membrane surface of the Xenopus Oocyte, so that histamine can be efficiently administered.

The electrophysiological measuring circuit 109 measures electric signals indicating the potential states and resistance states of the glass electrodes 102 and 103. Electric signals indicating the penetration of the cell membrane by the glass electrodes 102 and 103 are picked up by the electrophysiological measuring circuit 109, and the control computer 108 having recognized it sends back to the electrophysiological measuring circuit 109 a signal to fix the membrane potential to −60 mV, the membrane potential of the Xenopus Oocyte being thereby fixed.

After confirming the fixation of the membrane potential of the cell, the control computer 108 causes the microsyringe driving motor 125 to function to administer histamine, which is a ligand, to the histamine receptor expressed on the membrane surface of the Xenopus Oocyte with the microsyringe 126.

Incidentally, the receptor that can be expressed on the membrane surface of the Xenopus Oocyte is not limited to the histamine receptor, but various other receptors can as well be expressed. The histamine receptor present on the membrane surface of the Xenopus Oocyte is activated by combination with histamine, a series of signals are conveyed, and ultimately chlorite ions flow out of the cell from the chlorite channel of the Xenopus Oocyte.

The measurement recording computer 121 takes this chlorite ion flow as a variation in electric current and records it as such. After the measurement of one cell is completed, the control computer 108 releases fixation of the membrane potential through the electrophysiological measuring circuit 109, moves the glass electrode driving motors 104 and 105 to their respective initial positions, and pulls the two glass electrodes 102 and 103 off the Xenopus Oocyte. Then, the XY stage 101 is moved as long as the spacing to the adjoining cell, and the Xenopus Oocyte to be measured next is positioned at the center of the field of vision of the stereoscopic microscope 116. It is possible to automate the electrophysiological experiment on a plurality of Xenopus Oocytes efficiently and consecutively by repeating the procedure described so far.

Generally, in electrophysiometry using Xenopus Oocytes, a double electrode membrane voltage clamp method employing glass electrodes 102 and 103 is extensively applied. On the other hand, for smaller nerve cells than Xenopus Oocytes, a single electrode membrane voltage clamp method using only one glass electrode is extensively employed. This is because, while the ion amperage is measured at the pico-ampere level for nerve cells, a current in micro-amperes is generated in the larger cells of Xenopus Oocytes, making it difficult to apply the conventional single electrode membrane voltage clamp method as it is. However, as a matter of principle, it is possible to apply the single electrode membrane voltage clamp method even to the measurement of Xenopus Oocytes by designing an electric circuit capable of measuring a current of a few micro-amperes in terms of the ion current level expected in Xenopus Oocytes. This would result in simplification of the double electrode membrane voltage clamp method which entails the penetration of a plurality of glass electrodes, further making it possible to reduce errors. which the penetration of glass electrodes might involve. Since the procedure of measurement is similarly simplified, the single electrode membrane voltage clamp method permits measurement of more Xenopus Oocytes per unit length of time than the double electrode membrane voltage clamp method does, and the throughput is increased correspondingly. There is a further advantage of allowing a saving in the apparatus manufacturing cost.

Whereas micro-injection, which uses a glass capillary to inject the subject gene into cells manually, is one of the main streams of conventional techniques for introducing a gene into cells, the application of the method of this embodiment of the invention to penetrate a glass capillary into each cell by adding a mechanism to inject a fixed quantity of the gene into cells will make it possible to produce an apparatus for injecting a fixed quantity of the subject gene after automatically penetrating the glass capillary into each of a plurality of cells.

Figure 2:
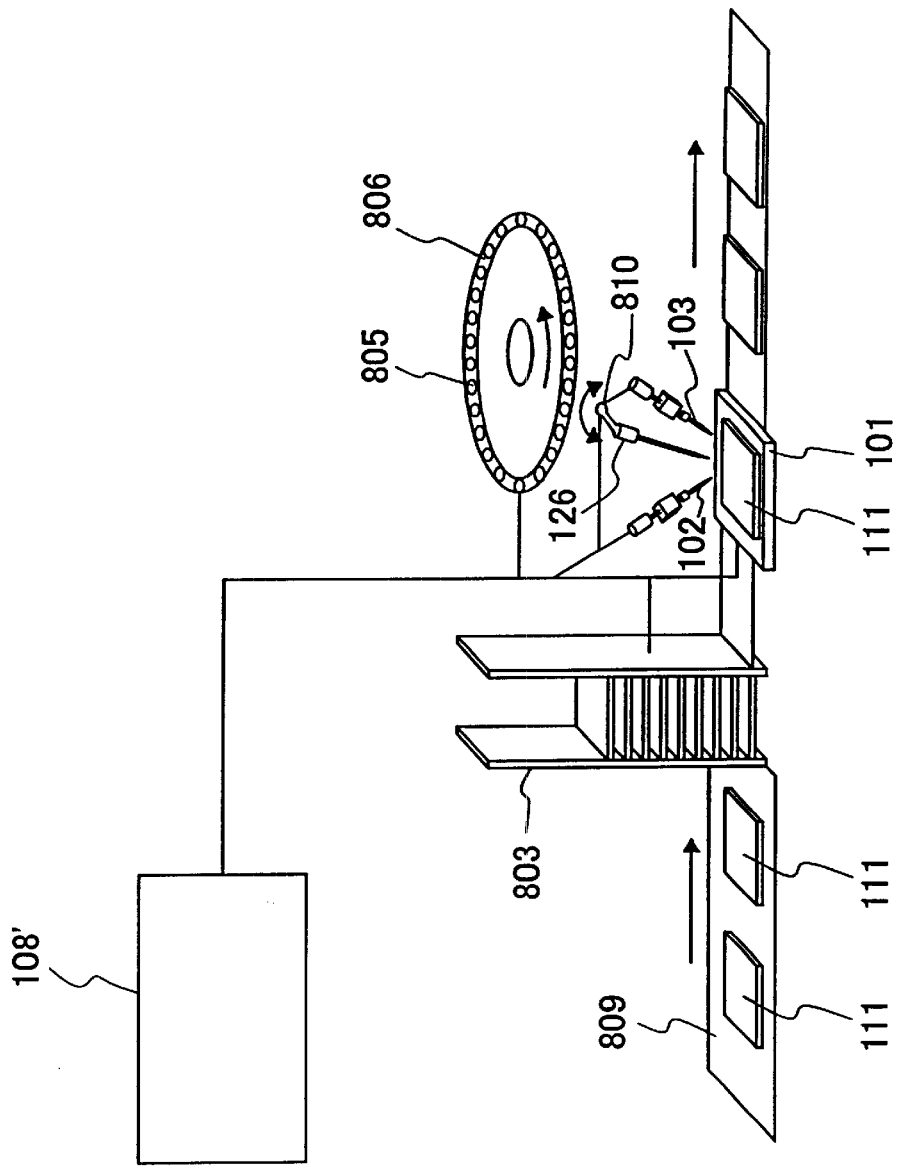
FIG. 2 illustrates an example of configuration of an automatic electrophysiological measuring apparatus embodying the invention for allergy diagnosis.

FIG. 2 illustrates an example of configuration of an automatic electrophysiological measuring apparatus embodying the invention for allergy diagnosis. A plurality of 96 well Xenopus Oocyte holding plates 111 are carried by a belt conveyor 809 and mounted on a plate stacker 803. By turning the plate stacker 803 a round, the plurality of 96 well Xenopus Oocyte holding plates 111 having been carried by the belt conveyor 809 are efficiently put in order, and the 96 well Xenopus Oocyte holding plates 111 can be smoothly fed to the XY stage 101 in succession. In the Xenopus Oocytes on each plate, the histamine receptor is already expressed.

What can be specifically cited as test subjects for allergy diagnosis include sugi (Japanese cedar), house dust and house ticks. An allergen is added in advance to blood extracted from each sample to be tested is incubated for 30 to 90 minutes, followed by centrifugal separation to collect the plasma content. This pretreatment is performed in advance. The plasma content from each sample is placed in a reaction container 805 in a reaction disk 806.

The plasma content in each reaction container 805 is picked up into the ligand administering microsyringe 126, which is then rotated by a motor 810 to administer the plasma content to the Xenopus Oocytes held in the 96 well Xenopus Oocyte holding cell 111. It is thereby made possible to test blood specimens taken from many sample bodies with respect to many test items. A control computer 108' carries out the foregoing actions in an integrated way. The control computer 108', besides controlling the motor drive controller 107 and the electrophysiological measuring circuit 109 (neither shown in FIG. 2 but shown in FIG. 1), also serves as the measurement recording computer 121 shown in FIG. 1 to collectively acquire and manage measured data.

Figure 3:
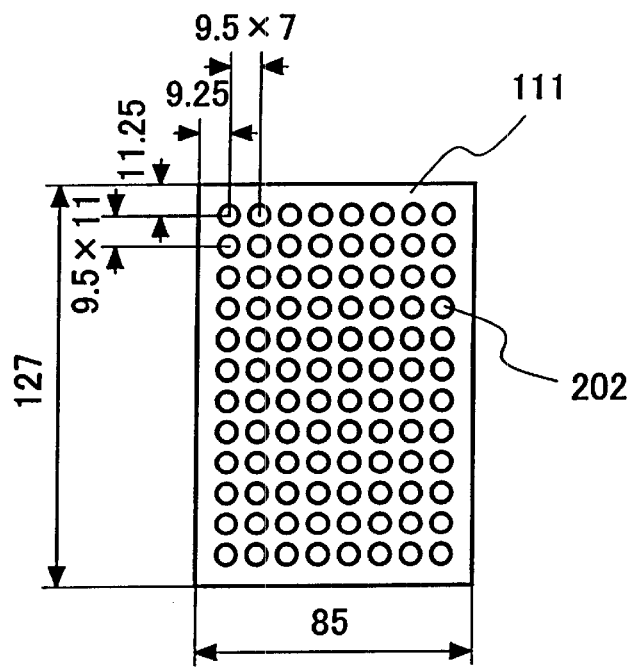
FIG. 3 is a plan of an example of configuration of each 96 well Xenopus Oocyte holding plate for use in the embodiment of the invention.
Figure 4:
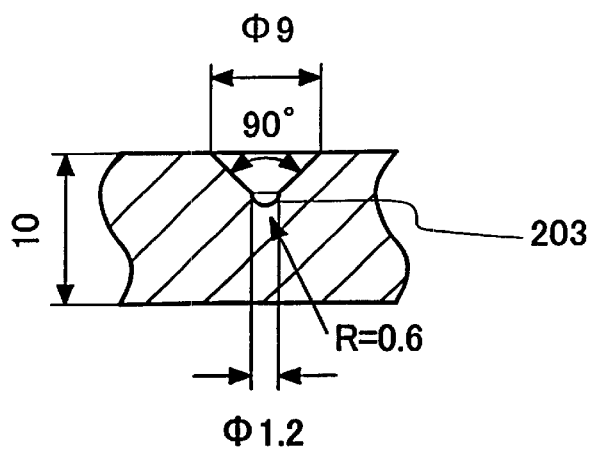
FIG. 4 shows a cross section of the 96 well Xenopus Oocyte holding plate illustrated in FIG. 3.

FIG. 3 is a plan of an example of configuration of each 96 well Xenopus Oocyte holding plate for use in the embodiment of the invention, and FIG. 4, a cross section of the 96 well Xenopus Oocyte holding plate illustrated in FIG. 3. The Xenopus Oocyte holding plate 111 has 8×12=96 independent cells 202. Each cell 202 is open upward at a 90 degree angle and has a semispherical part 203 at the bottom. Incidentally, the number of cells on a plate need not be limited to 96, but can be increased to 384, 864 or 1,536 depending on the size of cells to be used in the electrophysiological experiment.

Each of the cells 202 can and does hold one Xenopus Oocyte. Each of the Xenopus Oocyte holding plate 111 is as large as and has the same number of wells (cells) as a commercially available 96 well titer plate. The size of a Xenopus Oocyte holding plate 111 is 85 mm long, 127 mm wide and 10 mm thick. The diameter of a cell 202 is 9 mm, and the spacing between cells 202 is 9.5 mm.

The cell 202 can hold the Xenopus Oocyte in the semispherical part 203 at its bottom. If the diameter of this semispherical part 203 is too large, the Xenopus Oocyte cannot be stably held within the cell 202 when the glass electrodes 102 and 103 penetrate, but may move, making it impossible to let the glass electrodes 102 and 103 penetrate the Xenopus Oocyte. Or if the diameter of the semispherical part 203 is too small, the Xenopus Oocyte cannot be fully contained in the semispherical part 203 and accordingly cannot be stably held. The optimal diameter of the semispherical part 203 for stably holding the Xenopus Oocyte within the semispherical part 203 when the two glass electrodes 102 and 103 penetrate the Xenopus Oocyte is 1.2 mm±0.1 mm.

When the penetration of the glass electrodes 102 and 103 into the Xenopus Oocyte is to be visually observed with the stereoscopic microscope 116, the glass electrodes 102 and 103 cannot penetrate the Xenopus Oocyte in a direction normal to the Xenopus Oocyte holding plate 111. In this case, the glass electrodes 102 and 103 are required to have certain angles with respect to the vertical axis of the Xenopus Oocyte holding plate 111.

Figure 5:
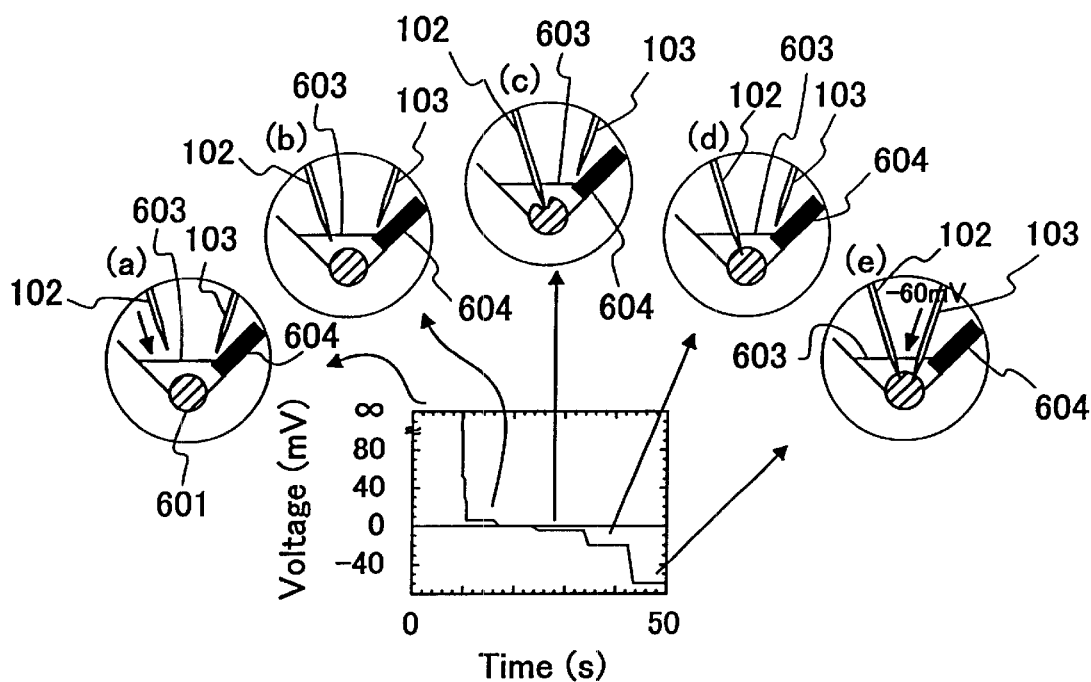
FIG. 5 illustrates how the penetration of the glass electrodes into the Xenopus Oocytes is controlled in the embodiment of the invention.

FIG. 5 illustrates how the penetration of the glass electrodes into the Xenopus Oocytes is controlled in the embodiment of the invention. According to the invention, the penetration of the glass electrodes into the Xenopus Oocytes is controlled on the basis of potential signals from the glass electrodes.

A Xenopus Oocytes 601 is held by one of the cells of the Xenopus Oocyte holding plate. The Xenopus Oocytes 601 is positioned on the axis of the movement of the glass electrodes 102 and 103. The ligand administering microsyringe 126 is adjusted to and installed in a position closely behind the glass electrode 103 (therefore not shown in FIG. 5). The graph in FIG. 5 shows how the potentials of the glass electrodes 102 and 103 vary over time, i.e. potential states from (a) through (e) corresponding to different positions of the glass electrodes.

As shown in (a), the glass electrode 102 is positioned above the solution surface 603, the grounding electrode 604 is not electrified, and accordingly the potential is infinite. The control computer, since the potential is infinite, recognizes the presence of the glass electrode 102 in the air.

As shown in (b), when the glass electrode 102 having begun to move toward the Xenopus Oocyte 601 arrives at the solution surface 603, the glass electrode 102 and the grounding electrode 604 become electrically connected via the solution 603 with the result that the potential comes to the vicinity of 0±3 mV. Having recognized the arrival of the glass electrode 102 at the solution surface 603, the control computer measures and determines whether or not the resistance of the glass electrode 102 falls within the permissible range of 0.8 MΩ to 2.4 MΩ. If the resistance of the glass electrode 102 is not within the permissible range, the glass electrode 102 is lifted by a motor and replaced. Further the control computer automatically removes an offset potential of ±3 mV and adjusts the potential to 0 mV.

As shown in (c), the control computer causes a motor to drive the glass electrode 102 toward the Xenopus Oocyte 601. As the glass electrode 102 comes into contact with the Xenopus Oocyte 601, the Xenopus Oocyte is elastically deformed. Then the potential of the glass electrode further drops by about 5 mV. Detecting this drop in potential, the control computer recognizes the coming into contact of the glass electrode 102 with the membrane surface of the Xenopus Oocyte 601.

As shown in (d), the control computer vibrates the glass electrode 102 on the drive shaft of the motor in a state in which the membrane surface of the Xenopus Oocyte 601 is placed under pressure. This enables the glass electrode 102 to penetrate the membrane smoothly without substantially damaging the Xenopus Oocyte 601. Since the usual membrane potential of the Xenopus Oocyte 601 is around −20 mV, the control computer recognizes the penetration of the glass electrode 102 into the Xenopus Oocyte 601 by detecting a potential of around −20 mV.

As shown in (e) the glass electrode 103 is also caused to penetrate the membrane of the Xenopus Oocyte 601 by repeating the actions of (a) through (d). After the two glass electrodes 102 and 103 have penetrated the Xenopus Oocyte 601, the control computer fixes the membrane potential at −60 mV by delivering a signal to fix the membrane potential at −60 mV to the electrophysiological measuring circuit 109.

As described in detail so far, this embodiment of the invention can penetrate the two glass electrodes 102 and 103 into Xenopus Oocytes 601 by using only the electric signals from the glass electrodes 102 and 103, and further can detect variations in electric current in response to the administration of histamine.

Next will be described below three different ways of grounding a 96 well Xenopus Oocyte holding plate 111 which is used in electrophysiological measurement.

Figure 6:
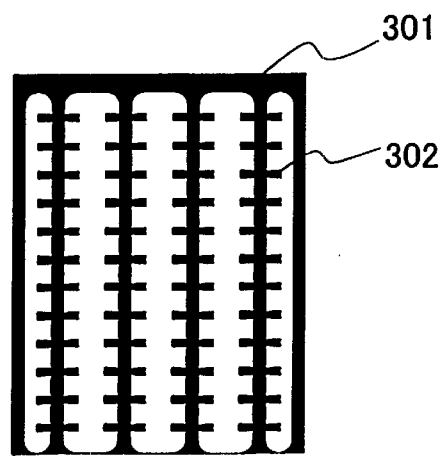
FIG. 6 is a plan showing the shape of the grounding electrode for the 96 well plate for use in the embodiment of the invention.
Figure 7:
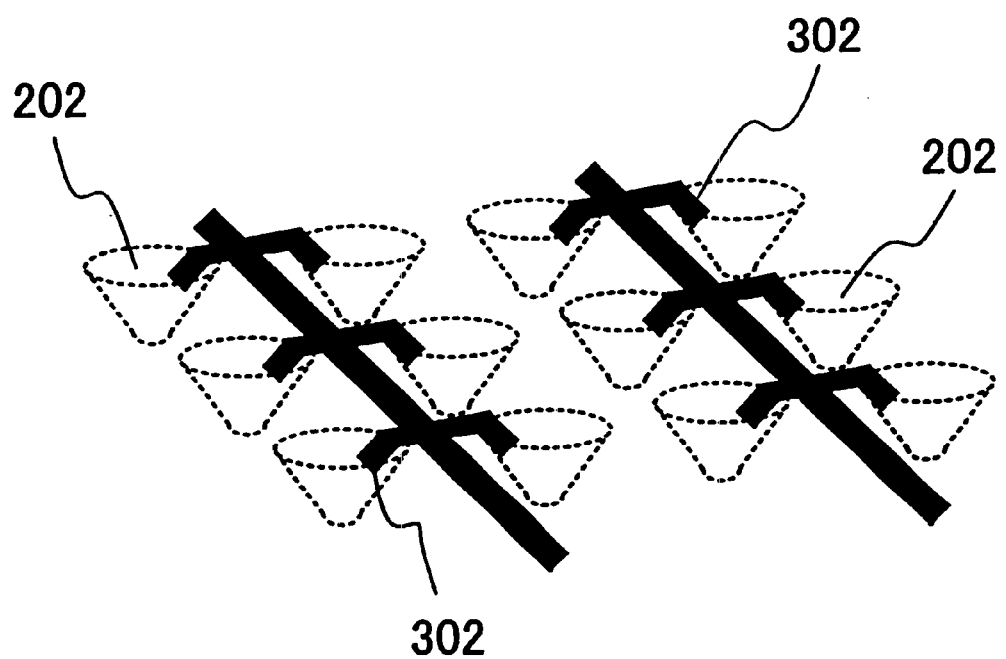
FIG. 7 is a partial perspective view of the grounding electrode for the 96 well Xenopus Oocyte plate holding shown in FIG. 6.

FIG. 6 is a plan showing the shape of the grounding electrode for the 96 well plate for use in the embodiment of the invention, and FIG. 7, a partial perspective view of the grounding electrode for the 96 well Xenopus Oocyte plate shown in FIG. 6. FIG. 6 illustrates a 96 well plate grounding electrode 301 to be combined with the 96 well Xenopus Oocyte holding plate 111. The 96 well plate grounding electrode 301, made of either copper or aluminum, is plated with silver after it is formed. Further, the silver-plated 96 well plate grounding electrode 301 is immersed in a 150 mM sodium chloride solution, and let stand for 24 hours or more under a D.C. of about 1.5 V to cause the silver and chlorine ions to react with each other and thereby to form a silver chloride capsule over the surface of the 96 well plate grounding electrode 301. Since the main constituent of the extracellular sap in living organisms is NaCl, if there is a chemical substance having ions common to the silver electrode and the NaCl solution (silver chloride in this case), the occurrence of any polarization voltage can be prevented so as to reduce electric noise affecting the measurement.

FIG. 7 shows a view of the 96 well plate grounding electrode 301 from obliquely above. The 96 well plate grounding electrode 301 has a grounding part 302 independently extending toward each of the cells 202, and the grounding part 302 is folded at a 45 degree angle along a side of the cell 202. For this reason, by grounding the 96 well plate grounding electrode 301 at one point, all the 96 cells 202 can be grounded. Besides the above-described method, it is also possible to directly pattern a grounding electrode on the 96 well Xenopus Oocyte holding plate 111 to ground it.

Figure 8:
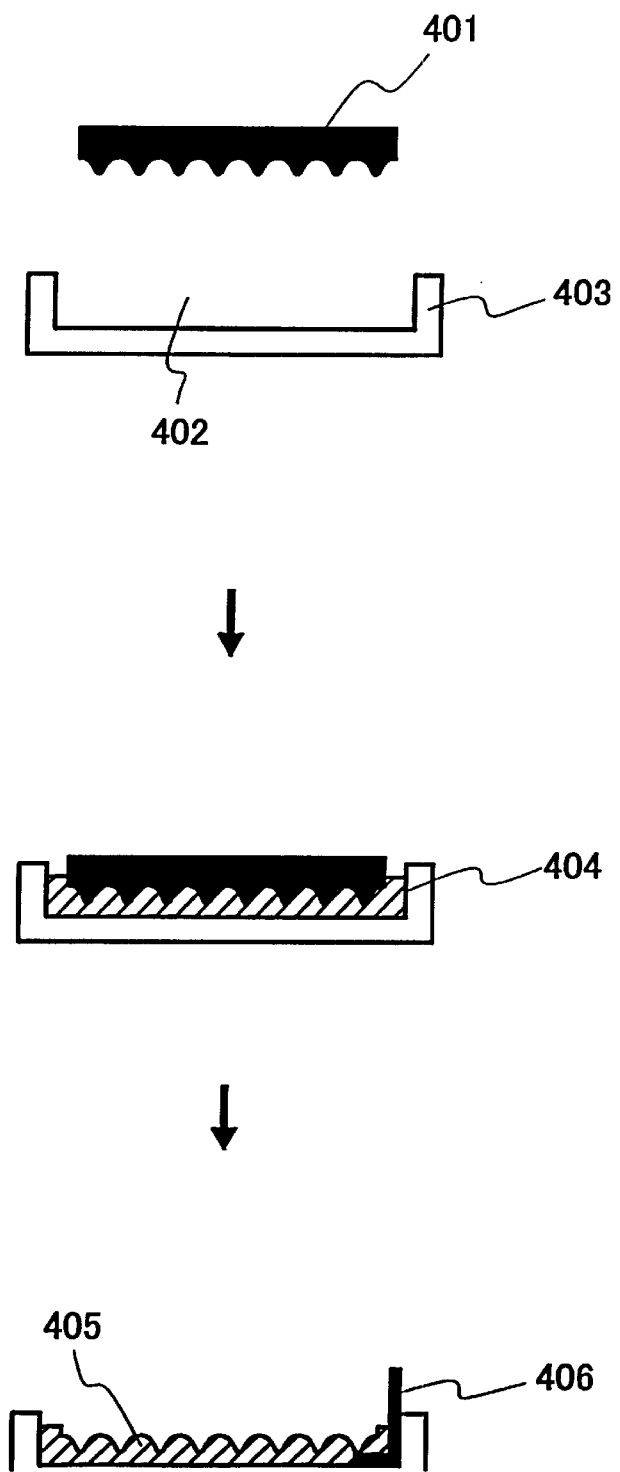
FIG. 8 illustrates how a 96 well Xenopus Oocyte holding plate consisting of agar for use in the embodiment of the invention is fabricated and grounded.

FIG. 8 illustrates how a 96 well Xenopus Oocyte holding plate consisting of agar for use in the embodiment of the invention is fabricated and grounded. According to the method described below, a Xenopus Oocyte holding plate consisting of agar is fabricated and grounded. Preheated agar 402 is poured into a container 403. Then a mold 401 for a 96 well Xenopus Oocyte holding cell is immersed in solated agar 402 and fixed. After being allowed to stand for a certain length of time, the solated agar 402 is cooled to room temperature and gelated. When the mold 401 is removed from the gelated agar 404, the gelated agar 404 is molded in a shape in which a Xenopus Oocyte can be held, so that a 96 well Xenopus Oocyte holding cell 405 consisting of agar can be fabricated. As the gelated agar 404 contains within the gel a sufficient quantity of aqueous solution to permit electrical continuity, the 96 individual cells can be collectively grounded by arranging the grounding electrode 406 in any convenient position on the agar. Therefore, by using the 96 well Xenopus Oocyte holding cell 405 consisting of agar in any convenient position on the agar, electrophysiological measurement can be consecutively carried out in a simple procedure without having to add any complex grounding electrode. The disposable agar-made container is far less expensive than a plastic-made container.

Figure 9:
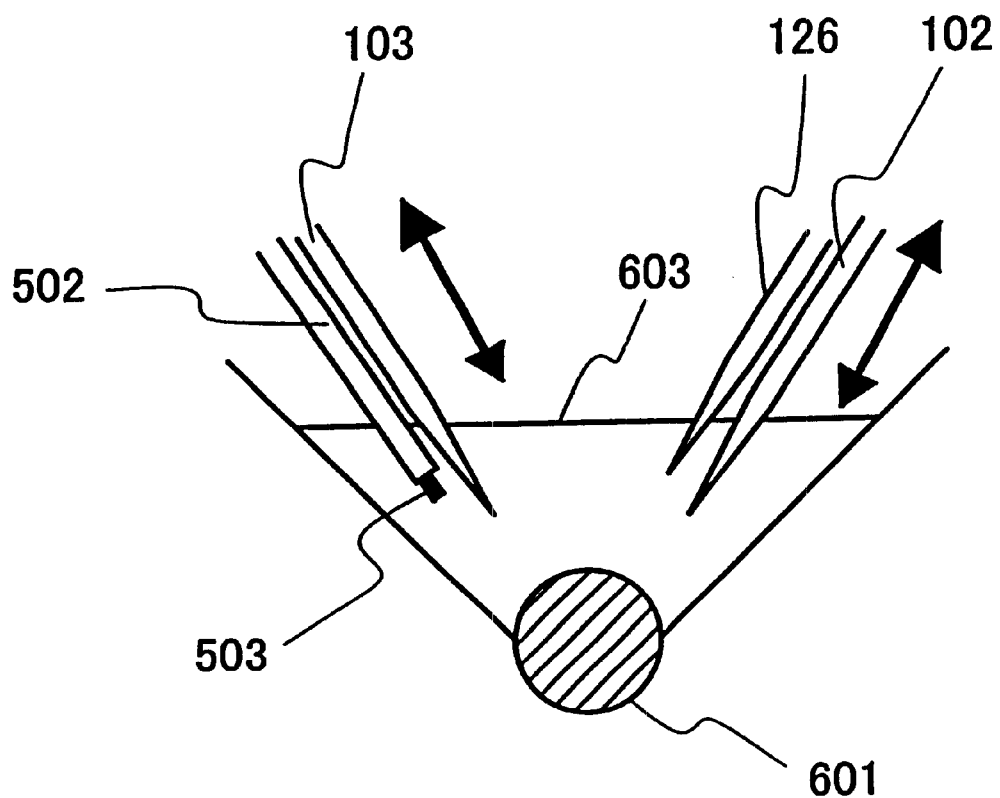
FIG. 9 illustrates an example of configuration for moving a grounding electrode in the embodiment of the invention and thereby grounding each cell.

FIG. 9 illustrates an example of configuration of moving a grounding electrode in the embodiment of the invention and thereby grounding each cell. As shown in FIG. 9, by causing the grounding electrode to move accompanying a glass electrode, grounding is accomplished by electrophysiometry in each cell. A grounding electrode 503 is fixed to near the tip of the glass electrode 103 via a support 502. The ligand administering microsyringe 126 is fixed in a form keeping an offset with respect to the glass electrode 102.

As the glass electrode 103 is moved toward the Xenopus Oocytes 601, the grounding electrode 503 comes into contact with the solution surface 603. The coming into contact of the grounding electrode 503 with the solution 603 establishes electrical continuity of the glass electrode 103, and the offset potential is removed. The glass electrode 102, too, can be similarly grounded. By causing the grounding electrode 503 to accompany the glass electrode 103, the plurality of cells can be stably grounded without having to add any complex grounding electrode. Alternatively, instead of causing the grounding electrode 503 to accompany the glass electrode 103, a grounding electrode driving motor can be newly provided to enable the grounding electrode 503 to independently move on a single axis. This brings the two glass electrodes, the grounding electrode and the ligand administering microsyringe very close to one another over the membrane surface of the Xenopus Oocyte at the time of administering histamine, the problem of susceptibility of measuring errors can be solved, and stable grounding is also made possible.

Figure 10:
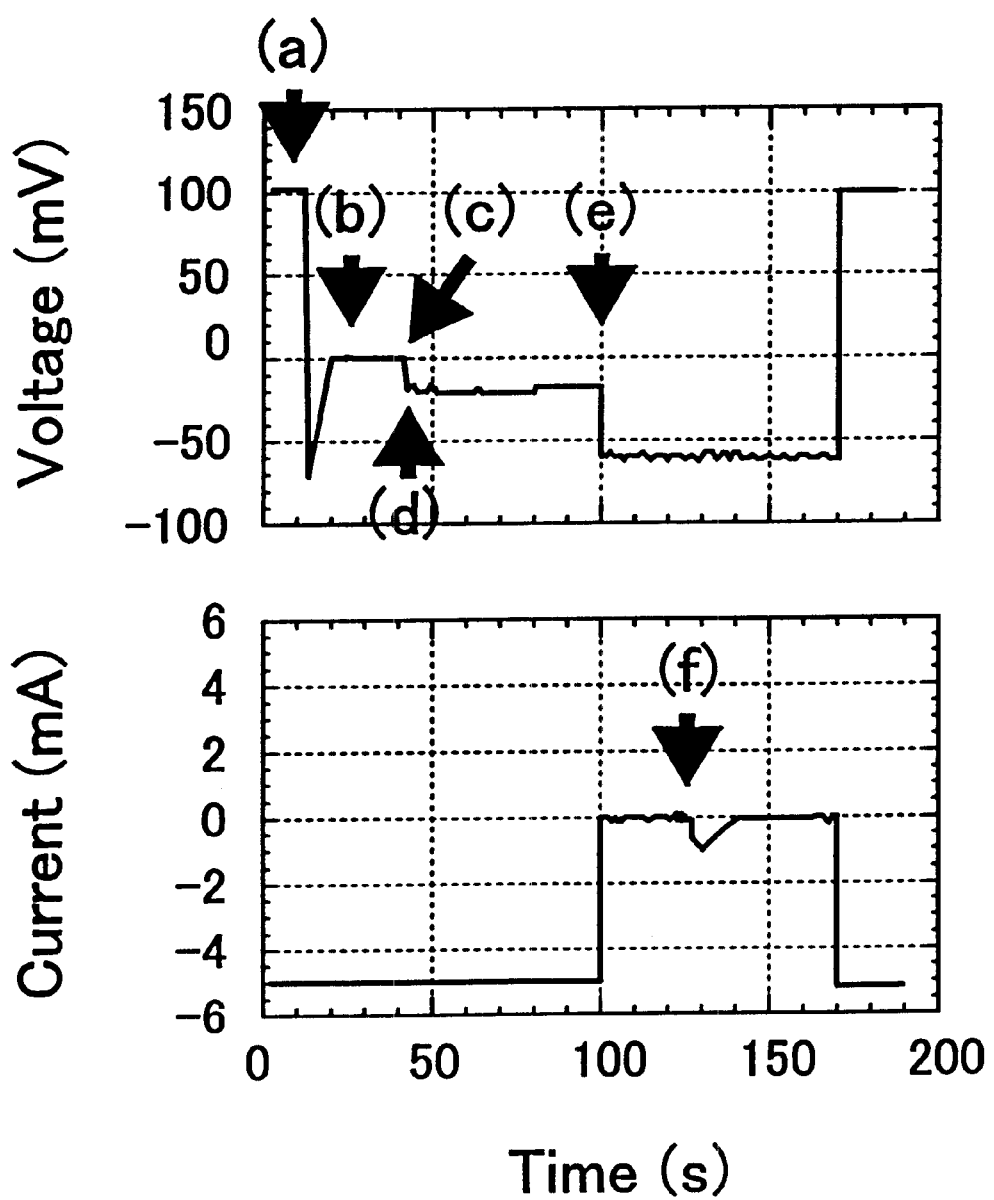
FIG. 10 shows experimental data representing reactions to the administration of histamine to Xenopus Oocytes using the automatic electrophysiological measuring apparatus embodying the invention.

FIG. 10 shows experimental data representing reactions to the administration of histamine to Xenopus Oocytes using the automatic electrophysiological measuring apparatus embodying the invention. FIG. 10 illustrates an example of automatic measurement of the result of histamine administration where the fixation of the membrane potential of the Xenopus Oocytes in which the histamine receptor is expressed in a fully automatic operation. The graph shows the findings of automatic measurement of responses to an electric current from the Xenopus Oocytes when, after the state of position changes of the glass electrode from (a) through (e) described with reference to FIG. 5 had been gone through, the membrane potential of the cell was fixed at the point of time indicated by arrow (e) and 5 $\mu$L (microliters) of 1 $\mu$M histamine was administered at the point of time indicated by arrow (f).

The measurement illustrated in FIG. 10 takes about 180 seconds per Xenopus Oocyte. However, this length of time required for measurement can be substantially shortened by such contrivances as the speeding of the movements of the glass electrodes and the stage and simultaneous penetration of the two glass electrodes into each Xenopus Oocyte. Moreover, while 20 seconds are spent to confirm the fixation of the membrane potential in the instance illustrated in FIG. 10, this can be dispensed with. Further, if only the concentration of histamine is to be measured, it will be sufficient to detect only the peak level (the current peak at the point where about 130 seconds have elapsed in the instance of FIG. 10) of the inward current that has arisen, but the measurement of history after the administration of histamine can be dispensed with. Therefore, measurement can be easily accelerated to take no more than 60 seconds per Xenopus Oocyte.

The automatic electrophysiological measuring apparatus according to the invention can penetrate fully automatically a glass electrode(s) into each of a plurality of Xenopus Oocytes in which a certain receptor is expressed by gene introduction, fix its potential, and measure the response to an electric current when the corresponding ligand is administered. As a result, for instance, allergy-related diagnoses can be made more speedily, and a large quantity of samples can be diagnosed in a short period of time. Furthermore, by automating the introduction of the gene of a seven-times transmembrane receptor whose function is unknown into Xenopus Oocytes and screening the ligand corresponding to the Xenopus Oocytes having expressed the unknown receptor, large-scale analysis of and search for the function of the gene can be accomplished efficiently.

The automatic electrophysiological measuring apparatus according to the invention can, by automating routine work, reduce the workload on the measuring personnel, enhance the speed of measurement and accomplish many measurement tasks in a short period of time, resulting in the acquisition of reliable data relatively free from fluctuations.

What is claimed is:

1. An automatic electrophysiological measuring method comprising a step to move a stage holding a container having a plurality of cells each holding a Xenopus Oocyte and position said Xenopus Oocyte in said cells; a step to penetrate a glass electrode(s) into said Xenopus Oocyte; a step to detect electric signals emitted from said glass electrode (s); a step to fix the membrane potential of said Xenopus Oocyte to a prescribed value; a step to administer a chemical substance to said Xenopus Oocyte; a step to carry out electrophysiological measurement on said Xenopus Oocyte; and a step to control the penetration of said glass electrode(s) into said Xenopus Oocyte, the fixation of the membrane potential of said Xenopus Oocyte and the administration of said chemical substance to said Xenopus Oocyte, wherein said controls are accomplished by detecting, on the basis of said electric signals emitted from said glass electrode(s), the contact of said glass electrode(s) with the solution surface in said cell and with the membrane surface of said Xenopus Oocyte and the penetration of said glass electrode(s) into the membrane of said Xenopus Oocyte.

* * * * *